(12) United States Patent
Hsiao

(10) Patent No.: US 9,078,938 B2
(45) Date of Patent: Jul. 14, 2015

(54) AROMATIC NEBULIZING DIFFUSER

(71) Applicant: SERENE HOUSE INTERNATIONAL ENTERPRISE LTD., Tortola (VG)

(72) Inventor: Ming Jen Hsiao, Miaoli (TW)

(73) Assignee: SERENE HOUSE INTERNATIONAL ENTERPRISE LTD., Tortola (VG)

( * ) Notice: Subject to any disclaimer, the term of this patent is extended or adjusted under 35 U.S.C. 154(b) by 302 days.

(21) Appl. No.: 13/840,006

(22) Filed: Mar. 15, 2013

(65) Prior Publication Data

US 2014/0263723 A1 Sep. 18, 2014

(51) Int. Cl.
*B05B 1/08* (2006.01)
*A61L 9/14* (2006.01)
*B05B 17/06* (2006.01)
*B05B 7/00* (2006.01)
*A61L 9/12* (2006.01)

(52) U.S. Cl.
CPC . *A61L 9/14* (2013.01); *A61L 9/122* (2013.01); *B05B 7/0012* (2013.01); *B05B 17/0615* (2013.01); *A61L 2209/132* (2013.01)

(58) Field of Classification Search
CPC .... B05B 17/06; B05B 17/0607; B05B 7/2405
USPC ................... 239/102.1, 102.2, 338
See application file for complete search history.

(56) References Cited

U.S. PATENT DOCUMENTS

| | | | | |
|---|---|---|---|---|
| 5,217,165 A | * | 6/1993 | Takahashi et al. | 239/102.2 |
| 5,299,739 A | * | 4/1994 | Takahashi et al. | 239/102.2 |
| 5,908,158 A | * | 6/1999 | Cheiman | 239/102.2 |
| 7,963,460 B2 | | 6/2011 | Jorgensen | |
| 7,992,801 B2 | | 8/2011 | Jorgensen | |
| 8,029,153 B2 | | 10/2011 | Jorgensen | |
| 8,133,440 B2 | | 3/2012 | Jorgensen | |
| 8,196,903 B2 | | 6/2012 | Jorgensen | |
| 8,296,993 B2 | * | 10/2012 | Modlin et al. | 43/132.1 |

* cited by examiner

*Primary Examiner* — Davis Hwu
(74) *Attorney, Agent, or Firm* — Ming Chow; Sinorica, LLC

(57) ABSTRACT

An aromatic nebulizing diffuser formed of a bottom holder shell, an electric fan, a mist creation block member, an oscillator, a circuit board, a power supply unit and a cover shell assembly is disclosed. The oscillator is adapted to oscillate an aromatic fluid in the mist creation block member into a mist of aromatic fluid droplets. The mist creation block member includes a semispherical air guide and a top flange, defining an air passage for guiding fan-induced currents of air to the nozzle hole of the cover shell assembly. The cover shell assembly defines a fluid storage chamber for providing a refill to the oscillation chamber, and a water stopper to prevent splashing.

12 Claims, 9 Drawing Sheets

AROMATIC NEBULIZING DIFFUSER

BACKGROUND OF THE INVENTION

1. Field of the Invention

The present invention relates to nebulizers and more particularly, to an aromatic nebulizing diffuser, which creates enhanced decorative and visual effects of aroma diffusion, and facilitates general maintenance and cleaning activities.

2. Description of the Related Art

With fast economic development and technological advancement and the rise of human civilization, there is a growing emphasis on the level of material and spiritual life, and having a good living environment has become the goal of people actively want to pursue. Further, air conditioners, air purifiers, fragrances, electric jasmines, aromatic nebulizing diffusers, perfume dispensers are intensively used in offices, rooms, cars, and many other living environments to eliminate bad smells and stale air, improving the work efficiency and mental health. Further, many new designs of aromatic nebulizing diffusers and perfume dispensers have been continuously created and have appeared on the market.

However, commercial aromatic nebulizing diffusers and perfume dispensers commonly have the following drawbacks:

1. Because the air guide conduct is mounted in the mist creation block member for guiding outside air into the mist creation block member, its size is limited, lowering the effect of pressurizing the intake flow of air. Further, the presence of the air guide conduct in the mist creation block member gives resistance to the intake flow of air, lowering the aroma diffusing effect, complicating the manufacturing process and increasing the manufacturing cost.
2. After a long use of an aromatic nebulizing diffuser or perfume dispenser, the internal components may be covered with oil stains. However, the complicated component mounting structure of a conventional aromatic nebulizing diffuser or perfume dispenser does not facilitate general maintenance and cleaning activities.
3. Because there is no any spare storage means adapted to give supply of an aromatic fluid or essential oil to the mist creation block member, the mist creation block member must be maximized to hold a large amount of aromatic fluid or essential oil, and the oscillator needs to oscillate a large amount of aromatic fluid or essential oil in the mist creation block member into a mist of aromatic fluid droplets, lowering the aroma diffusing effect.
4. During oscillation of the oscillator to oscillate the aromatic fluid or essential oil into a mist of aromatic fluid droplets, the contained aromatic fluid or essential oil may be partially forced out of the mist creation block member, causing aromatic fluid/essential oil loss or contaminating the outer surfaces of the aromatic nebulizing diffuser or perfume dispenser. Further, the splashed fluid can hinder the flowing of the created mist of aromatic fluid droplets, lowering the aroma diffusing effect.

Therefore, it is desirable to provide an aromatic nebulizing diffuser, which eliminates the aforesaid drawbacks.

SUMMARY OF THE INVENTION

The present invention has been accomplished under the circumstances in view. It is main object of the present invention to provide an aromatic nebulizing diffuser, which enhances the aroma diffusing effect. It is another object of the present invention to provide an aromatic nebulizing diffuser, which facilitates mounting and dismounting and general maintenance and cleaning activities. It is still another object of the present invention to provide an aromatic nebulizing diffuser, which can gives refills to the oscillation chamber. It is still another object of the present invention to provide an aromatic nebulizing diffuser, which prevents the supplied aromatic fluid from splashing out of the oscillation chamber.

To achieve these and other objects of the present invention, an aromatic nebulizing diffuser comprises a bottom holder shell comprising an accommodation open chamber and a plurality of air vents in communication with the accommodation open chamber, an electric fan mounted in the accommodation open chamber and operable to suck outside air through the air vents into the accommodation open chamber, a mist creation block member mounted in the bottom holder shell to seal a top open side of the accommodation open chamber, the mist creation block member comprising an oscillation chamber adapted for holding an aromatic fluid, a through hole located in a bottom side of the oscillation chamber, a semispherical air guide disposed therein and defining an air hole in communication with said accommodation open chamber of said bottom holder shell, a top flange surrounding the semispherical air guide and a notch located in the top flange and facing toward the oscillation chamber for guiding currents of air induced by electric fan into the oscillation chamber, an oscillator sealed in the through hole of the oscillation chamber of the mist creation block member and adapted to oscillate an aromatic fluid in the oscillation chamber into a mist of aromatic fluid droplets, a circuit board electrically coupled with the oscillator, a power supply unit electrically connected to the electric fan, the oscillator and the circuit board to provide the electric fan, the oscillator and the circuit board with the necessary working voltage, and a cover shell assembly detachably mounted at the bottom holder shell to shield the mist creation block member. The cover shell assembly comprises an upper cover shell and a lower cover shell. The upper cover shell comprises a nozzle hole and a top guide tube. The lower cover shell comprises a bottom guide tube connected to the top guide tube. Thus, the nozzle hole, the top guide tube, the bottom guide tube and the oscillation chamber provide a passage for guiding a created mist of aromatic fluid droplets out of the oscillation chamber to the outside open air.

Preferably, the bottom guide tube defines an air passage hole in communication with the notch in the top flange.

Preferably, the bottom holder shell comprises a step located on the inside thereof, and a water seal ring squeezed in between said mist creation block member and said step.

Preferably, an oscillator sealing gasket ring is mounted in the through hole of the oscillation chamber of the mist creation block member to seal the oscillator in the through hole, and a locating plate is bonded to the oscillation chamber to seal the oscillator sealing gasket ring in the through hole of the oscillation chamber.

Preferably, the aromatic nebulizing diffuser further comprises a functional keypad mounted in the accommodation open chamber of the bottom holder shell. The functional keypad comprises a circuit board electrically coupled to the oscillator, the oscillator circuit board and the power supply unit, and a plurality of key switches electrically connected to the circuit board for functional controls.

Preferably, the lower cover shell is abutted against the top flange in such a manner that a side-open air guide chamber is defined between the semispherical air guide and the top flange.

Preferably, the upper cover shell defines a rounded recess in the top wall thereof around the nozzle hole.

Preferably, the cover shell assembly defines a fluid storage chamber between the upper cover shell and the lower cover shell for accommodation a fluid for giving a refill to the oscillation chamber.

Preferably, the lower cover shell comprises a locating hole in communication between the fluid storage chamber and the oscillation chamber, and a water valve mounted in the locating hole and switchable to open/close the locating hole. The water valve comprises a valve block fastened to the locating hole, a valve stem movably mounted in the valve block, a spring mounted around the valve stem and stopped between one end of the valve stem and a part of the valve block, and a rubber flap fastened to an opposite end of the valve stem and movable with the valve stem to close/open the locating hole. The oscillation chamber comprises a protrusion stoppable against the valve stem to keep the rubber flap away from the valve block for allowing the locating hole to communicate the fluid storage chamber and the oscillation chamber.

Preferably, the cover shell assembly further comprises a water stopper mounted in the top guide tube. The water stopper comprises a ring-shaped member fixedly mounted in the top guide tube, a rib rack fixedly mounted in the ring-shaped member, a plurality of open spaces defined in the rib rack, and a smoothly arched baffle plate connected to the rib rack and suspending below the ring-shaped member.

Preferably, the lower cover shell comprises a bottom coupling flange of outer diameter slightly smaller than the inner diameter of the top rim of the bottom holder shell. Thus, the bottom coupling flange of the top cover shell assembly can be directly and detachably press-fitted into the top rim of the bottom holder shell.

Other advantages and features of the present invention will be fully understood by reference to the following specification in conjunction with the accompanying drawings, in which like reference signs denote like components of structure.

DETAILED DESCRIPTION OF THE PREFERRED EMBODIMENT

Figure 1:
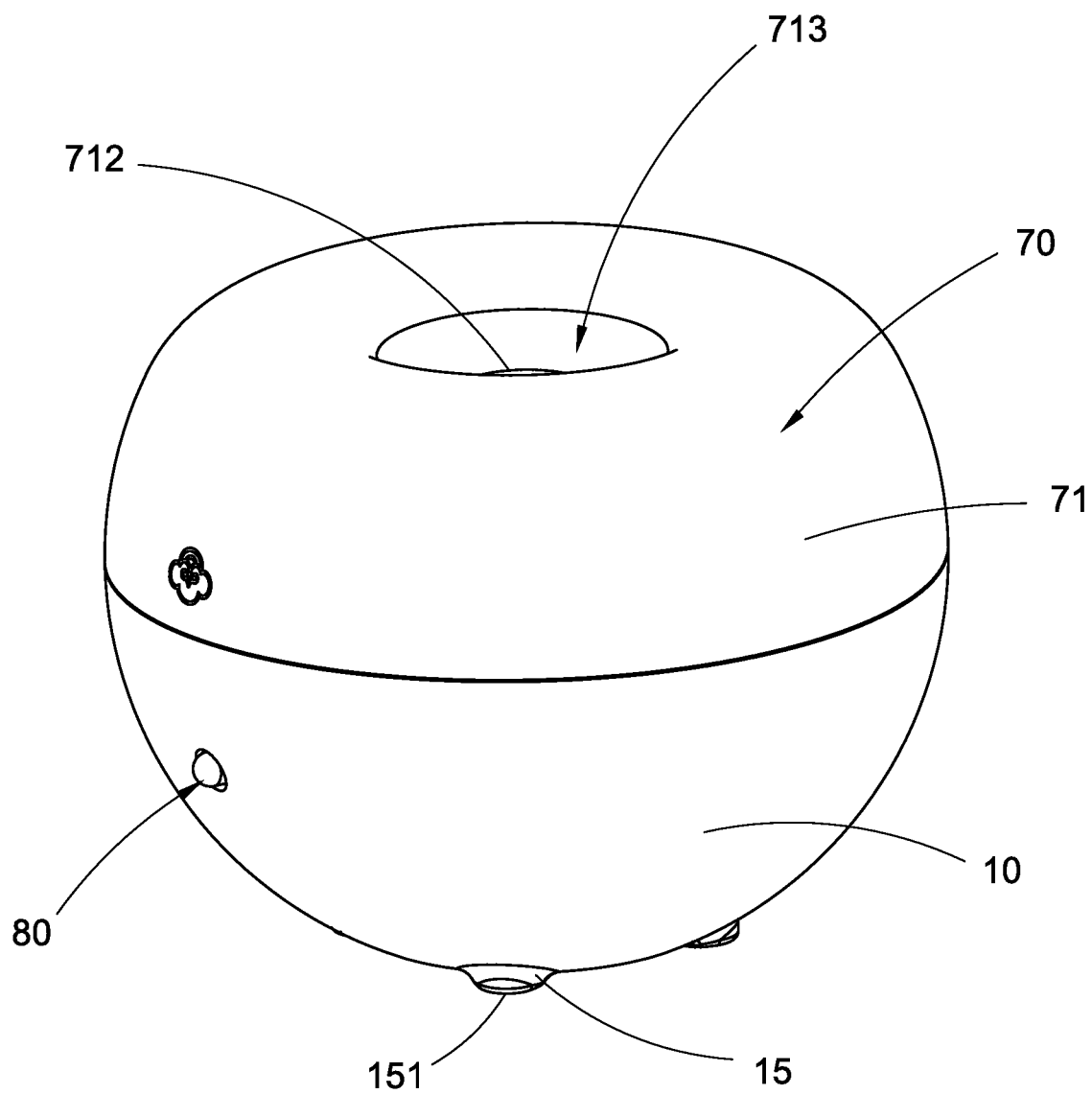
FIG. 1 is an elevational view of an aromatic nebulizing diffuser in accordance with the present invention.
Figure 2:
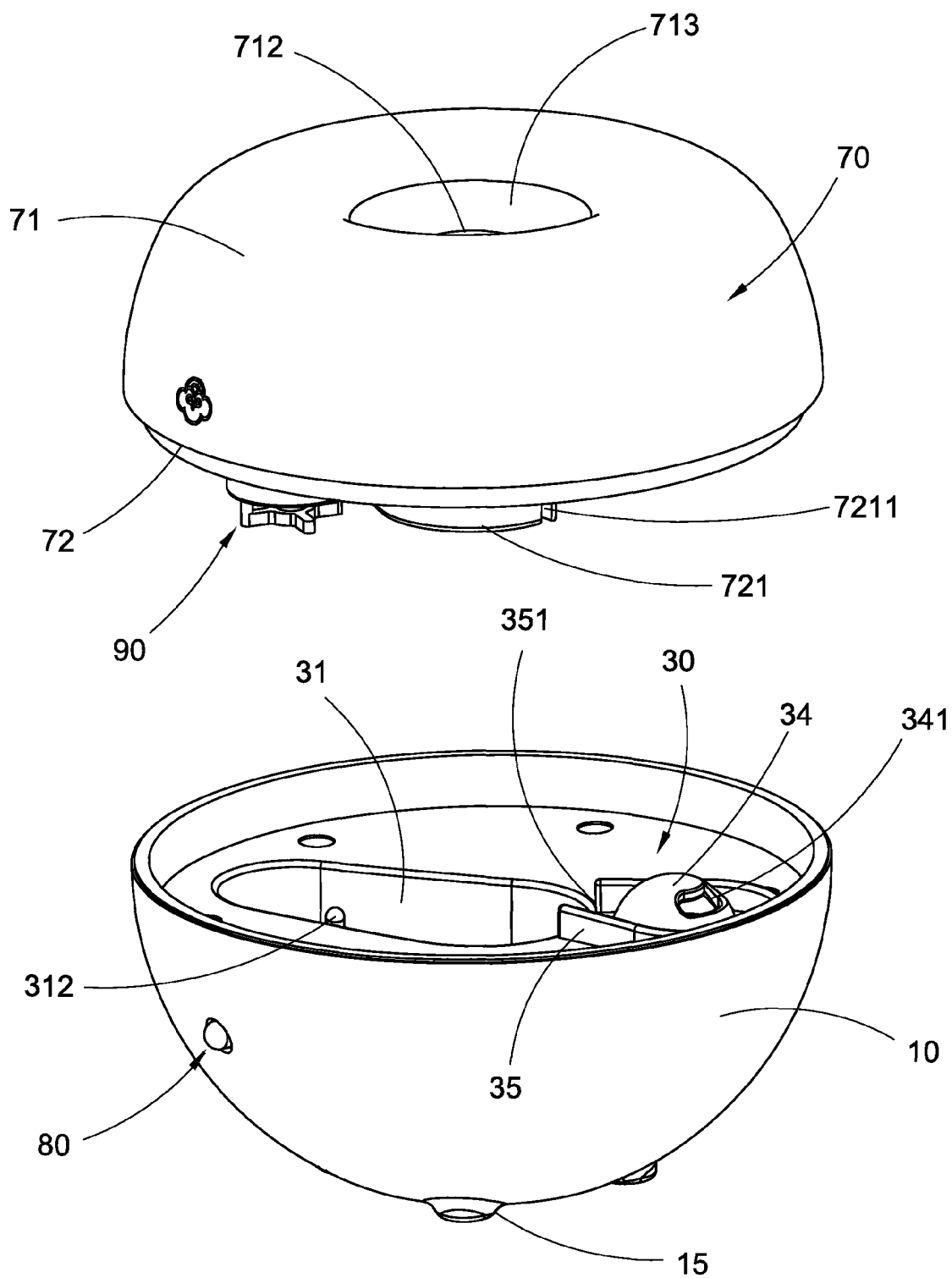
FIG. 2 is an exploded view of the cover shell assembly of the aromatic nebulizing diffuser in accordance with the present invention.
Figure 3:
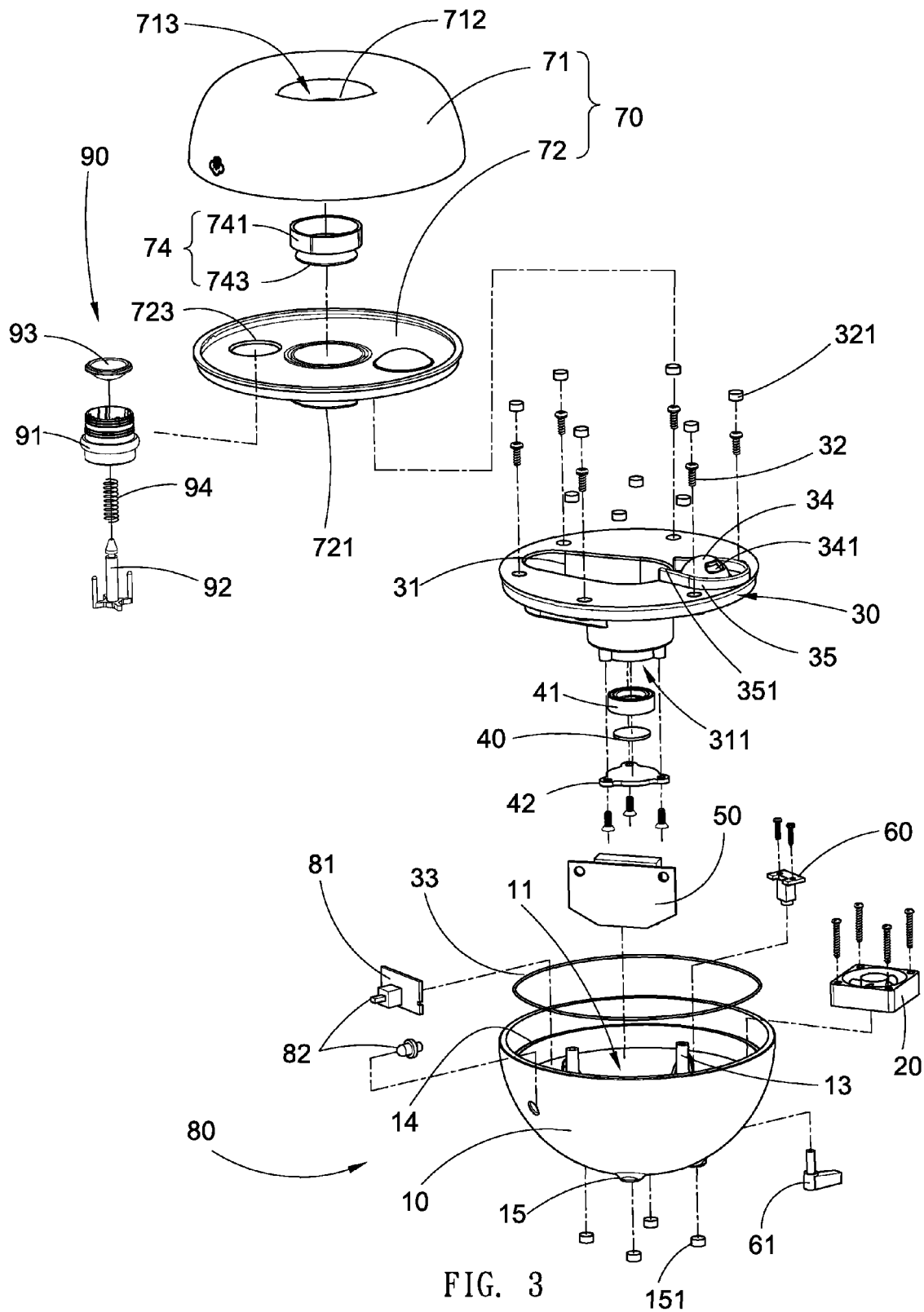
FIG. 3 is an exploded view of the aromatic nebulizing diffuser in accordance with the present invention.

Referring to FIGS. 1, 2 and 3, an aromatic nebulizing diffuser in accordance with the present invention is shown. The aromatic nebulizing diffuser comprises a bottom holder shell 10, an electric fan 20, a mist creation block member 30, an oscillator 40, an oscillator circuit board 50, a power supply unit 60, and a top cover shell assembly 70. The mist creation block member 30 is designed to provide an oscillation chamber and flow guide means to facilitate intake of air and to enhance the nebulizing effect. The coupling structure between the bottom holder shell 10 and the top cover shell assembly 70 facilitates mounting and dismounting and general maintenance and cleaning activities. The top cover shell assembly 70 is capable of storing an extra amount of aromatic fluid for making a refill, and can prevent splashing and nozzle hole blockage.

Figure 4:
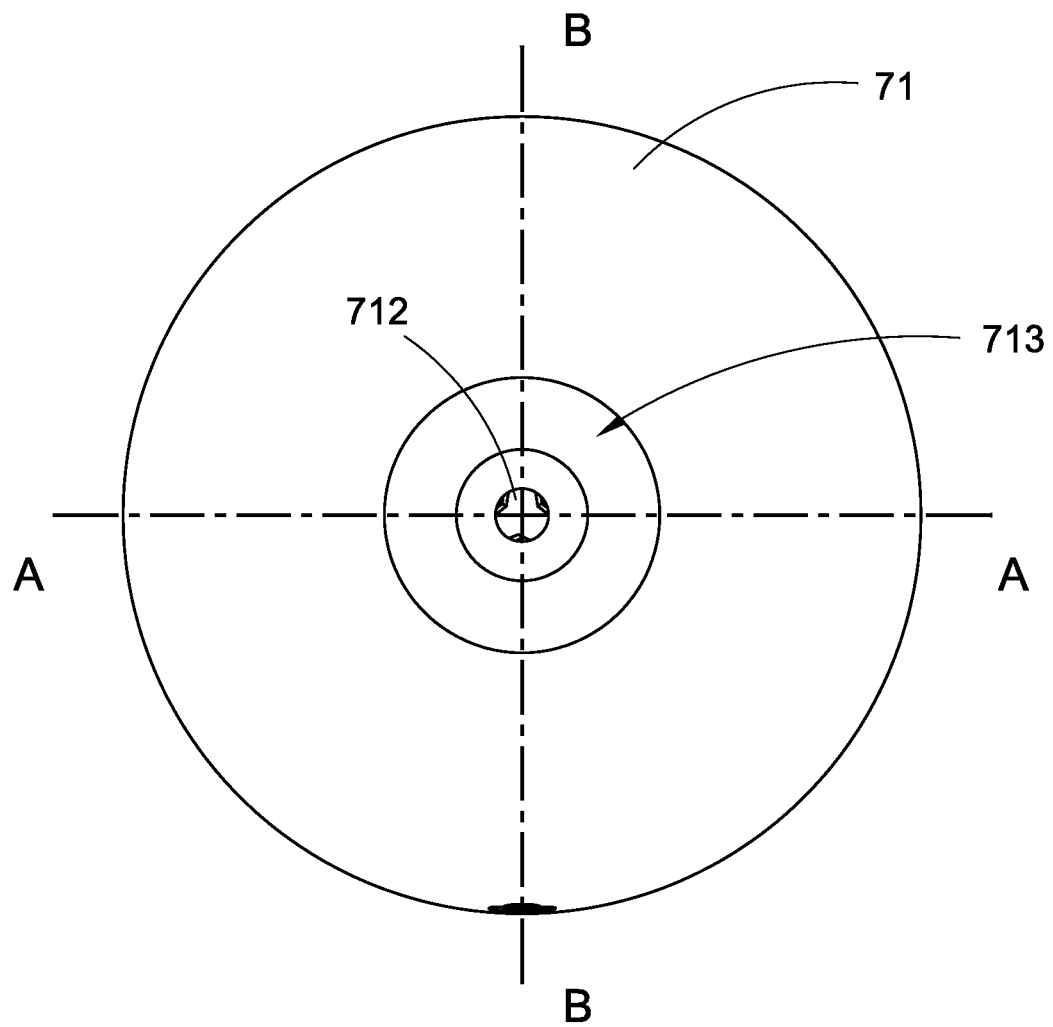
FIG. 4 is a top view of the aromatic nebulizing diffuser in accordance with the present invention.
Figure 7:
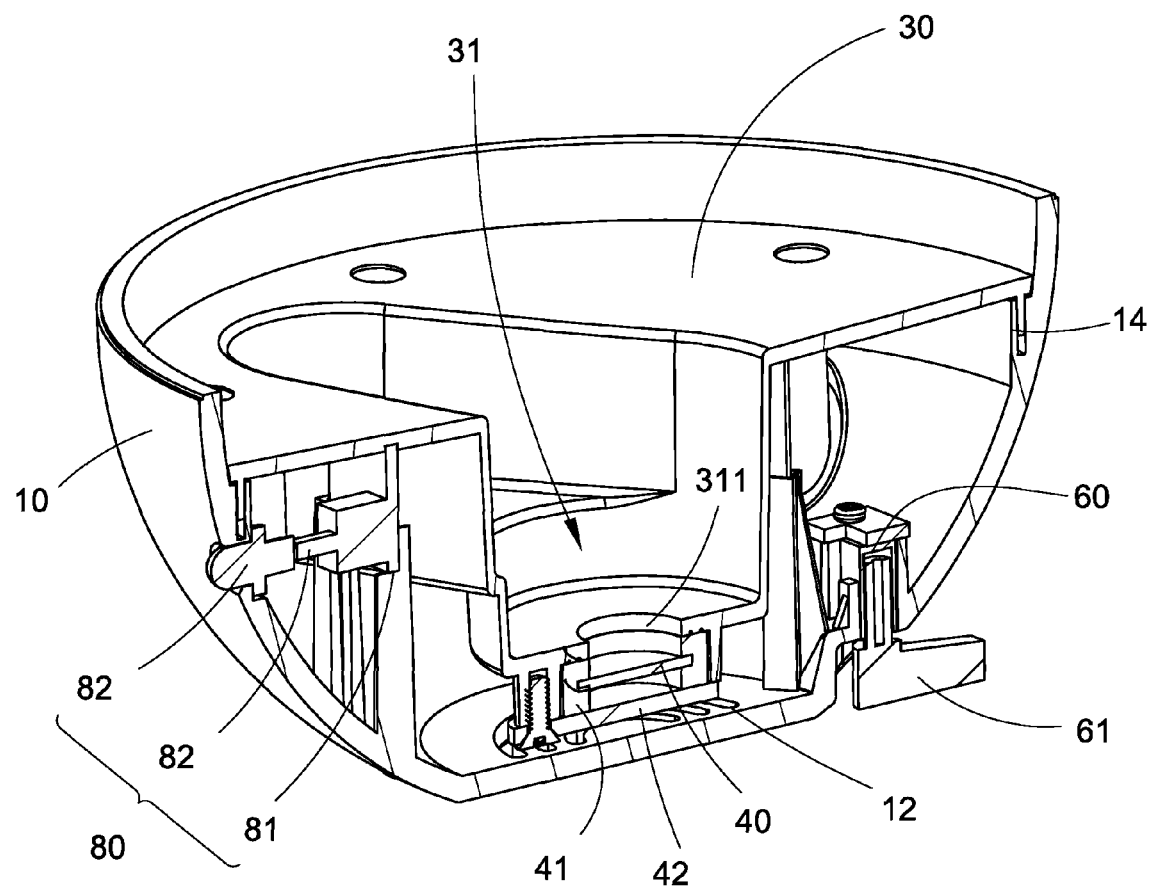
FIG. 7 is a sectional elevation of the bottom holder shell taken along line B-B of FIG. 4.

Referring to FIGS. 4 and 7, and FIGS. 2 and 3 again, the bottom holder shell 10 comprises an accommodation open chamber 11, a plurality of air vents 12 located on the bottom side thereof in communication between the accommodation open chamber 11 and the atmosphere for taking in outside air, a plurality of columns 13 and a step 14 disposed inside the accommodation open chamber 11, and a plurality of foot members 15 fixedly mounted at the bottom side thereof and respectively equipped with a rubber pad 151 for supporting the bottom holder shell 10 stably on a flat surface. Referring to FIGS. 3, 4 and 7 again, the electric fan 20 is mounted in the accommodation open chamber 11 and operable to suck outside air through the air vents 12 into the inside of the accommodation open chamber 11.

Figure 5:
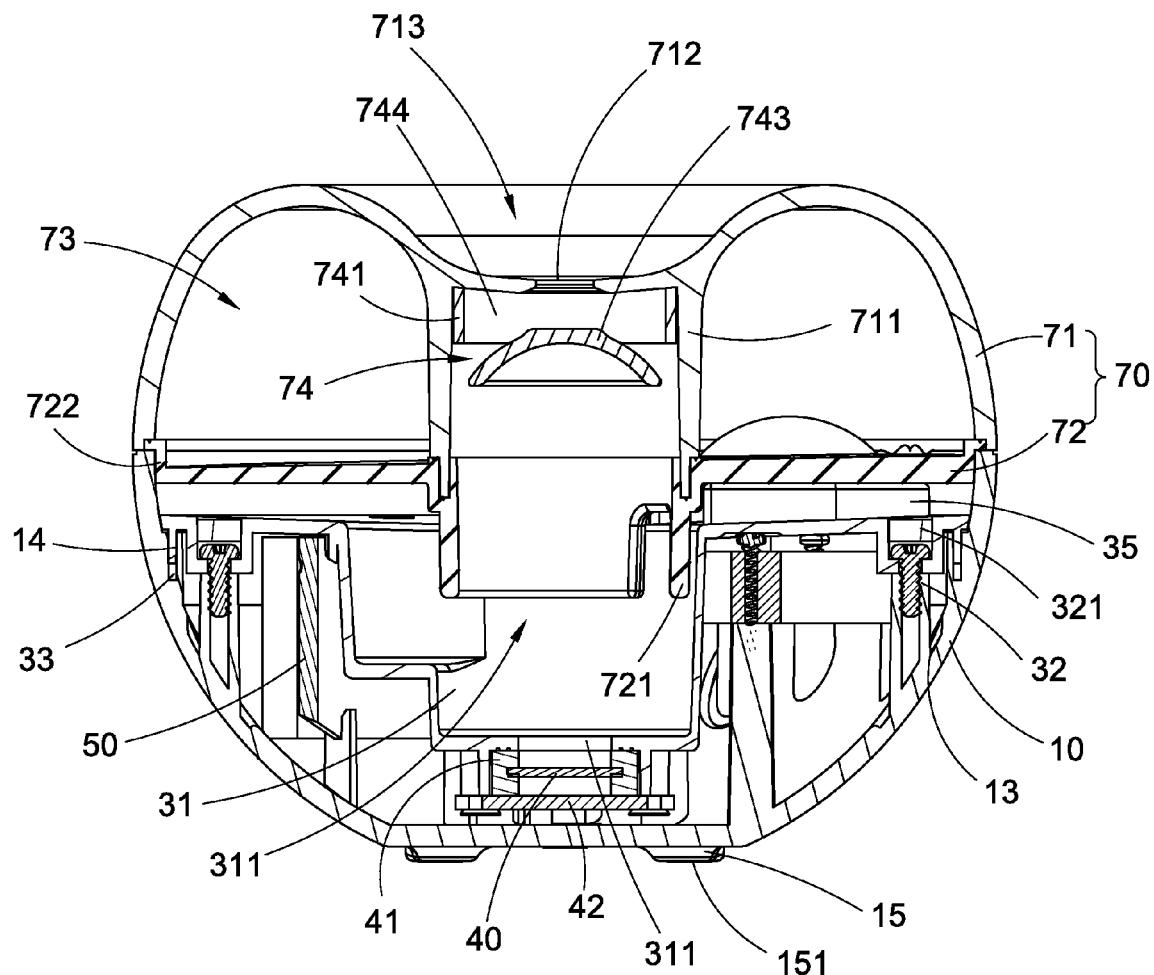
FIG. 5 is a sectional elevation taken along line A-A of FIG. 4.

Referring to FIG. 5 and FIGS. 2-4 again, the mist creation block member 30 is an one-piece member (for example, made out of a plastic material by injection molding) fixedly fastened to the columns 13 of the bottom holder shell 10 by fastening members, for example, screws 32, defining therein an oscillation chamber 31 where an aromatic fluid (for example, a mixture of an essential oil and water) can be oscillated into a mist of aromatic fluid droplets, and a bottom through hole 311 cut through the bottom wall thereof in communication between the oscillation chamber 31 and the accommodation open chamber 11. Decorative plugs 321 are fastened to the top wall of the mist creation block member 30 in a flush manner to keep the screws 32 from sight. Further, a water seal ring 33 is squeezed in between the mist creation block member 30 and the step 14 of the bottom holder shell 10 to seal the accommodation open chamber 11. Further, a semispherical air guide 34 is mounted in a top side of the mist creation block member 30, defining an air hole 341 in communication with the accommodation open chamber 11. The mist creation block member 30 further comprises a top flange 35 protruded from the top wall thereof and extending around the semispherical air guide 34, and a notch 351 formed in the top flange 35 and facing toward the oscillation chamber 31. The semispherical air guide 34, the top flange 35 and the notch 351 form an air guide structure for guiding currents of air induced by the electric fan 20 into the oscillation chamber 31 and a nozzle hole 712 of the top cover shell assembly 70.

Referring to FIGS. 3, 4, 5 and 7 again, the oscillator 40 is mounted within a gasket ring 41 in the bottom through hole 311 of the mist creation block member 30, and then a locating plate 42 is affixed to the bottom side of the mist creation block member 30 to seal the bottom through hole 311 and to hold the oscillator 40 in the bottom through hole 314 within the gasket ring 41. Thus, the oscillator 40 can be operated to oscillate an aromatic fluid in the oscillation chamber 31 into a mist of aromatic fluid droplets.

The oscillator circuit board 50 is mounted in the accommodation open chamber 11 and electrically coupled with the oscillator 40 for driving the oscillator 40 to oscillate an aromatic fluid in the oscillation chamber 31 into a mist of aerosol droplets.

Referring to FIGS. 3, 4 and 7 again, the power supply unit 60 is mounted in the accommodation open chamber 11 and electrically connected to the electric fan 20, the oscillator 40 and the oscillator circuit board 50. Preferably, the bottom holder shell 10 is equipped with a port for enabling an external power plug 61 to be connected to the power supply unit 60 to provide an external power supply to the electric fan 20, the oscillator 40 and the oscillator circuit board 50.

Figure 6:
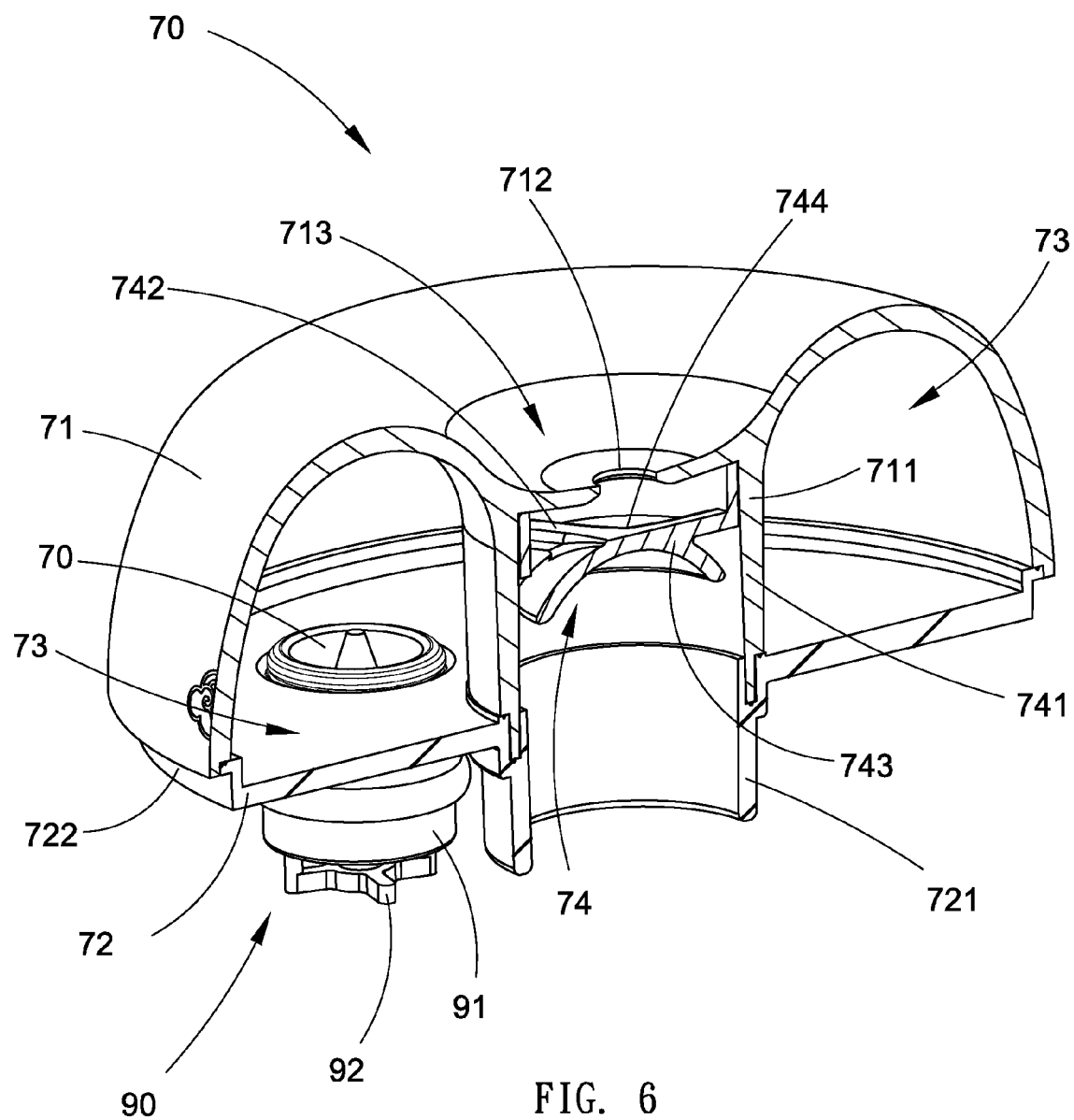
FIG. 6 is a sectional elevation of the cover shell assembly taken along line B-B of FIG. 4.

Referring to FIG. 6 and FIGS. 2-5 again, the top cover shell assembly 70 is covered on the top side of the bottom holder shell 10 to shield the mist creation block member 30, comprising an upper cover shell 71, a lower cover shell 72. The upper cover shell 71 comprises a top guide tube 711 and a nozzle hole 712. The lower cover shell 72 comprises a bottom guide tube 721 defining therein an air passage hole 7211. The nozzle hole 712, the top guide tube 711, the bottom guide tube 721 and the oscillation chamber 31 are kept in communication with one another, providing a passage for guiding the created mist of aromatic fluid droplets from the oscillation chamber 31 to the atmosphere.

The lower cover shell 72 has its bottom surface abutted against the top flange 35 so that a side-open air guide chamber is defined between the semispherical air guide 34 and the top flange 35. Further, the air passage hole 7211 of the lower cover shell 721 is kept in communication with the notch 351 in the top flange 35 so that the fan-induced currents of air can go through the air hole 341, the notch 351 in the top flange 35 and the air passage hole 7211 of the bottom guide tube 721 into the oscillation chamber 31 and the nozzle hole 712.

The upper cover shell 71 defines a rounded recess 713 at the top wall thereof around the nozzle hole 712 for enabling the ejected mist of aromatic fluid droplets to be widely diffused into the outside open air, enhancing the decorative and visual effects of aroma diffusion.

Referring to FIG. 1 again, the cover shell assembly 70 is configured to fit the bottom holder shell 10, exhibiting the shape of a flower bud and enhancing the decorative and visual effects of aroma diffusion.

Referring to FIGS. 1, 3, 4 and 7 again, the invention further comprises a functional keypad 80 mounted in the accommodation open chamber 11 of the bottom holder shell 10. The functional keypad 80 comprises a circuit board 81 electrically coupled to the oscillator 40, the oscillator circuit board 50 and the power supply unit 60, and a plurality of key switches 82 electrically connected to the circuit board 81 for situational lighting options, time setting, power control and other related functional controls. The bottom holder shell 10 has means, for example, holes for accommodating the key switches 82.

Referring to FIGS. 3-5 again, after understanding of the component parts of the aromatic nebulizing diffuser and their positioning, the operation and features of the aromatic nebulizing diffuser will now be outlined hereinafter. At first, the user needs to fill an aromatic fluid (for example, an essential oil and water mixture) into the oscillation chamber 31 of the mist creation block member 30. Thereafter, the user can turn on the oscillator 40 and the electric fan 20, causing the oscillator 40 to oscillate the aromatic fluid into a mist of aromatic fluid droplets and the electric fan 20 to suck outside air through the air vent 12 of the bottom holder shell 10 and the air hole 341 of the semispherical air guide 34 into the side-open air guide chamber between the semispherical air guide 34 and the top flange 35 and then into the oscillation chamber 31 via the notch 351 to further carrying the created mist of aromatic fluid droplets out of the top cover shell assembly 70 into the outside open air via the nozzle hole 712.

Referring to FIGS. 2 and 3 again, the coupling structure between the bottom holder shell 10 and the cover shell assembly 70 facilitates general maintenance and cleaning activities. The lower cover shell 72 of the top cover shell assembly 70 comprises a bottom coupling flange 722 of outer diameter slightly smaller than the inner diameter of the top rim of the bottom holder shell 10. Thus, the bottom coupling flange 722 of the top cover shell assembly 70 can be directly and detachably press-fitted into the top rim of the bottom holder shell 10.

Figure 8:
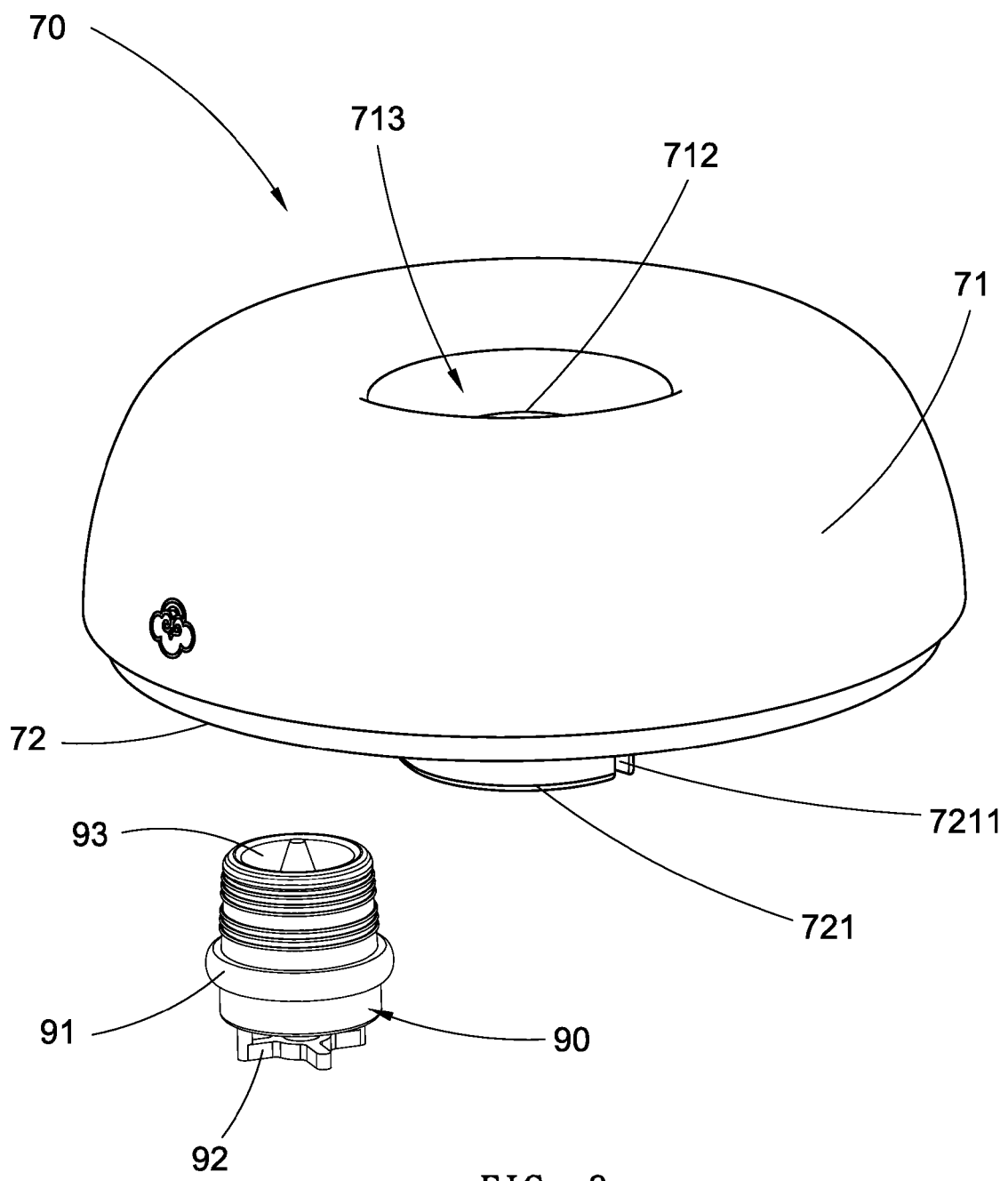
FIG. 8 is an exploded view of the cover shell assembly and water valve of the aromatic nebulizing diffuser in accordance with the present invention.
Figure 9:
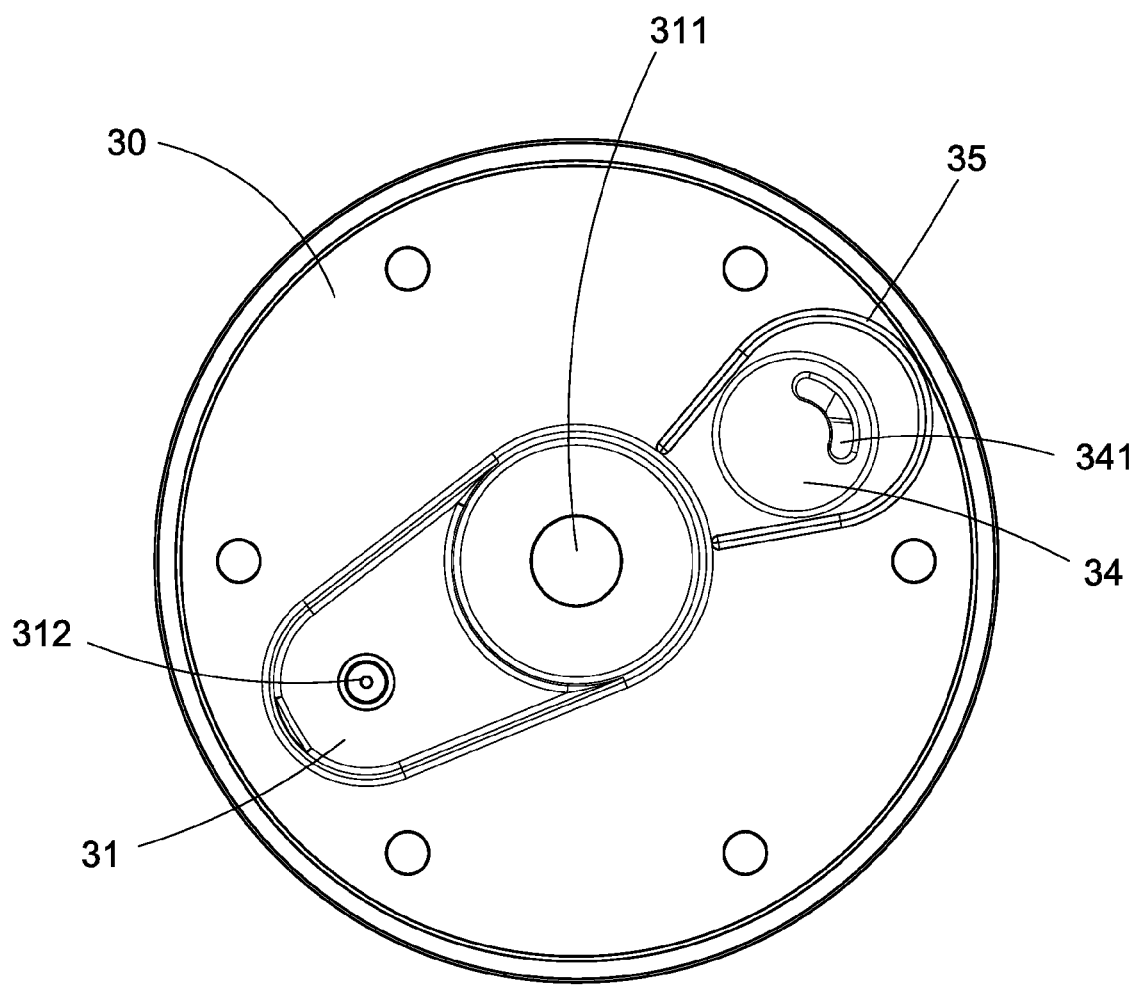
FIG. 9 is a top view of the bottom holder shell of the aromatic nebulizing diffuser in accordance with the present invention.

Referring to FIGS. 8 and 9 and FIGS. 3, 4, 5 and 6 again, a fluid storage chamber 73 is defined within the cover shell assembly 70 between the upper cover shell 71 and the lower cover shell 72 around the top guide tube 711 for storing a fluid, for example, water.

The lower cover shell 72 further comprises a locating hole 723, and a water valve 90 mounted in the locating hole 723 switchable between an open position and a close position to control the supply of the storage fluid from the fluid storage chamber 73 to the oscillation chamber 31.

Subject to the design of the semispherical air guide 34 and top flange 35 of the mist creation block member 30 to provide a passage for enabling the electric fan 20 to induce currents of air into the oscillation chamber 31, it is not necessary to provide any extra air guide means in the oscillation chamber 31, and supplying air to the oscillation chamber 31 will not encounter any resistance. Further, using the fluid storage chamber 73 to supply water to the oscillation chamber 31, the volume of the oscillation chamber 31 can be minimized. During application, it simply needs to apply a small amount of water and essential oil to the oscillation chamber 31 for quick oscillation, enhancing aroma diffusion efficiency and effects.

The water valve 90 comprises a valve block 91, a valve stem 92, a rubber flap 93 and a spring 94. The valve block 91 is a hollow member thread-connected to the locating hole 723 of the lower cover shell 72. The valve stem 92 is movably inserted into the valve block 91. The spring 94 is mounted on the valve stem 92 and stopped between one end of the valve stem 92 and an inside part of the valve block 91. The rubber flap 93 is closely attached to the top open side of the valve block 91 to prohibit flowing of the storage fluid out of the fluid storage chamber 73 through the valve block 91.

Referring to FIGS. 2, 3 and 9, the oscillation chamber 31 further comprises a protrusion 312. After connection between the cover shell assembly 70 and the bottom holder shell 10, the valve step 92 of the water valve 90 is stopped against the protrusion 312 to lift the rubber flap 93 away from the top open side of the valve block 91, allowing the fluid to flow from the fluid storage chamber 73 to the oscillation chamber 31. On the contrary, after separation between the protrusion 312 and the water valve 90, the water valve 90 is closed, stopping the supply of the fluid from the fluid storage chamber 73.

Thus, when the fluid in the oscillation chamber 31 reaches a predetermined high level, the valve block 91 is closed, the fluid communication between the fluid storage chamber 73 and the water valve 90 is interrupted, and the storage fluid in the fluid storage chamber 73 cannot be guided into the oscillation chamber 31. On the contrary, when the aromatic fluid level drops due to working of nebulizing diffusion in the oscillation chamber 31, the aromatic fluid does not block the valve block 91, and the storage fluid is guided out of the fluid storage chamber 73 into the oscillation chamber 31 again. Thus, the above fluid refilling action is repeated again and again, improving the drawbacks of prior art designs that cannot give a refill to the oscillation chamber.

Further, because the cover shell assembly 70 can store a liquid, a relatively smaller oscillation chamber 31 can be used to hold an aromatic fluid (mixture of water and essential oil).

Further, because the volume of the oscillation chamber 31 is smaller than the volume of the fluid storage chamber 73, the oscillator 40 can oscillate the aromatic fluid in the oscillation chamber 31 into a mist of aromatic fluid droplets efficiently and rapidly, shortening the waiting time. In order to get a better nebulizing diffusion performance, the volume of the oscillation chamber 31 must be smaller than the fluid storage chamber 73.

Referring to FIGS. 3-6 again, the cover shell assembly 70 further comprises a water stopper 74 mounted in the top guide tube 711. The water stopper 74 comprises a ring-shaped member 741 fixedly mounted in the top guide tube 711, a rib rack 742 fixedly mounted in the ring-shaped member 741, a plurality of open spaces 744 defined in the rib rack 742, and a smoothly arched baffle plate 743 connected to the rib rack 742 and suspending below the ring-shaped member 741.

Thus, the water stopper 74 can prevent the aromatic fluid from splashing out of the oscillation chamber 31 to block the nozzle hole 712, allowing the created mist of aromatic fluid droplets to fly through the open spaces 744 in the top guide tube 711 and the nozzle hole 712 to the outside open air.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. An aromatic nebulizing diffuser, comprising:
a bottom holder shell comprising an accommodation open chamber and a plurality of air vents in communication with said accommodation open chamber;
an electric fan mounted in said accommodation open chamber and operable to suck outside air through said air vents into said accommodation open chamber;
a mist creation block member mounted in said bottom holder shell to seal a top open side of said accommodation open chamber, said mist creation block member comprising an oscillation chamber adapted for holding an aromatic fluid, a through hole located in a bottom side of said oscillation chamber, a semispherical air guide disposed therein, said semispherical air guide defining an air hole in communication with said accommodation open chamber of said bottom holder shell, a top flange surrounding said semispherical air guide, and a notch located in said top flange and facing toward said oscillation chamber for guiding currents of air induced by electric fan into said oscillation chamber;
an oscillator sealed in said through hole of said oscillation chamber of said mist creation block member and adapted to oscillate an aromatic fluid in said oscillation chamber into a mist of aromatic fluid droplets;
a circuit board electrically coupled with said oscillator;
a power supply unit electrically connected to said electric fan, said oscillator and said circuit board to provide said electric fan, said oscillator and said circuit board with the necessary working voltage; and
a cover shell assembly detachably mounted at said bottom holder shell to shield said mist creation block member, said cover shell assembly comprising an upper cover shell and a lower cover shell, said upper cover shell comprising a nozzle hole and a top guide tube, said lower cover shell comprising a bottom guide tube connected to said top guide tube, said nozzle hole, said top guide tube, said bottom guide tube and said oscillation chamber providing a passage for guiding a created mist of aromatic fluid droplets out of said oscillation chamber to the outside open air.

2. The aromatic nebulizing diffuser as claimed in claim 1, wherein said bottom guide tube defines an air passage hole in communication with said notch in said top flange.

3. The aromatic nebulizing diffuser as claimed in claim 1, wherein said bottom holder shell comprises a step located on the inside thereof, and a water seal ring squeezed in between said mist creation block member and said step.

4. The aromatic nebulizing diffuser as claimed in claim 2, wherein said bottom holder shell comprises a step located on the inside thereof, and a water seal ring squeezed in between said mist creation block member and said step.

5. The aromatic nebulizing diffuser as claimed in claim 1, further comprising an oscillator sealing gasket ring mounted in said through hole of said oscillation chamber of said mist creation block member to seal said oscillator in said through hole, and a locating plate bonded to said oscillation chamber to seal said oscillator sealing gasket ring in said through hole of said oscillation chamber.

6. The aromatic nebulizing diffuser as claimed in claim 1, further comprising a functional keypad mounted in said accommodation open chamber of said bottom holder shell, said functional keypad comprising a circuit board electrically coupled to said oscillator, said oscillator circuit board and said power supply unit, and a plurality of key switches electrically connected to said circuit board for functional controls.

7. The aromatic nebulizing diffuser as claimed in claim 1, wherein said lower cover shell is abutted against said top flange in such a manner that a side-open air guide chamber is defined between said semispherical air guide and said top flange.

8. The aromatic nebulizing diffuser as claimed in claim 1, wherein said upper cover shell defines a rounded recess in a top wall thereof around said nozzle hole.

9. The aromatic nebulizing diffuser as claimed in claim 1, wherein said cover shell assembly defines a fluid storage chamber between said upper cover shell and said lower cover shell for accommodation a fluid for giving a refill to said oscillation chamber.

10. The aromatic nebulizing diffuser as claimed in claim 1, wherein said lower cover shell comprises a locating hole in communication between a fluid storage chamber in said cover shell assembly and said oscillation chamber, and a water valve mounted in said locating hole and switchable to open/close said locating hole, said water valve comprising a valve block fastened to said locating hole, a valve stem movably mounted in said valve block, a spring mounted around said valve stem and stopped between one end of said valve stem and a part of said valve block, and a rubber flap fastened to an opposite end of said valve stem and movable with said valve stem to close/open said locating hole; said oscillation chamber comprises a protrusion stoppable against said valve stem to keep said rubber flap away from said valve block in opening said locating hole.

11. The aromatic nebulizing diffuser as claimed in claim 9, wherein said lower cover shell comprises a locating hole in communication between said fluid storage chamber and said oscillation chamber, and a water valve mounted in said locating hole and switchable to open/close said locating hole, said water valve comprising a valve block fastened to said locating hole, a valve stem movably mounted in said valve block, a spring mounted around said valve stem and stopped between one end of said valve stem and a part of said valve block, and a rubber flap fastened to an opposite end of said valve stem and movable with said valve stem to close/open said locating hole; said oscillation chamber comprises a protrusion stoppable against said valve stem to keep said rubber flap away from said valve block for allowing said locating hole to communicate said fluid storage chamber and said oscillation chamber.

12. The aromatic nebulizing diffuser as claimed in claim 1, wherein said cover shell assembly further comprises a water stopper mounted in said top guide tube, said water stopper comprising a ring-shaped member fixedly mounted in said top guide tube, a rib rack fixedly mounted in said ring-shaped member, a plurality of open spaces defined in said rib rack, and a smoothly arched baffle plate connected to said rib rack and suspending below said ring-shaped member.

\* \* \* \* \*